United States Patent
Matuschek et al.

(10) Patent No.: US 7,314,739 B2
(45) Date of Patent: Jan. 1, 2008

(54) LIPASE VARIANTS

(75) Inventors: Markus Matuschek, Weinheim (DE); Rainer Stürmer, Rödersheim-Gronau (DE); Bernhard Hauer, Fußgönheim (DE); Gerhard Klebe, Marburg (DE); Marco Bocola, Hückeswagen (DE)

(73) Assignee: BASF Aktiengesellschaft (DE)

( * ) Notice: Subject to any disclaimer, the term of this patent is extended or adjusted under 35 U.S.C. 154(b) by 458 days.

(21) Appl. No.: 10/493,210

(22) PCT Filed: Oct. 17, 2002

(86) PCT No.: PCT/EP02/11620

§ 371 (c)(1),
(2), (4) Date: Apr. 21, 2004

(87) PCT Pub. No.: WO03/035878

PCT Pub. Date: May 1, 2003

(65) Prior Publication Data

US 2005/0255571 A1   Nov. 17, 2005

(30) Foreign Application Priority Data

Oct. 22, 2001 (DE) ............... 101 51 292
Feb. 8, 2002 (DE) ............... 102 05 444

(51) Int. Cl.
*C12P 7/62* (2006.01)
*C12P 7/40* (2006.01)
*C12N 9/20* (2006.01)
*C12N 1/20* (2006.01)
*C12N 15/00* (2006.01)
*C07H 21/04* (2006.01)

(52) U.S. Cl. ............ 435/135; 435/136; 435/198; 435/252.3; 435/320.1; 536/23.2

(58) Field of Classification Search ......... 435/135, 435/136, 198, 252.3, 320.1; 536/23.2
See application file for complete search history.

(56) References Cited

U.S. PATENT DOCUMENTS 6,551,806 B1   4/2003 Stürmer
6,596,520 B1   7/2003 Friedrich et al.

FOREIGN PATENT DOCUMENTS

| EP | 1 069 183 A2 | 1/2001 |
|---|---|---|
| WO | WO92/05249 | 4/1992 |
| WO | WO95/35381 | 12/1995 |
| WO | WO 00/05354 | 2/2000 |

OTHER PUBLICATIONS

M. Nardin, et al., "Crystal Structure of *Pseudomonas aeruginosa* Lipase in the Open Conformation," *J. Biol. Chem.*, vol. 275, No. 40, Oct. 6, 2003, pp. 31219-31225.
K. Liebeton, et al., "Directed Evolution of an Enantioselective Lipase," *Chemistry and Biology*, vol. 7, 2000, pp. 709-718.
L. G. J. Frenken, et al., "Cloning of the *Pseudomonas glumae* Lipase Gene and Determination of the Active Site Residues," *Applied and Environm. Microbiology*, vol. 58, No. 12, 1992, pp. 3787-3791.
J. L. Arpigny, et al., "Bacterial Lipolytic Enzymes: Classification and Properties," *Biochem. J.*, vol. 343, 1999, pp. 177-183.
Hwang, B-Y., et al., "Computer-aided molecular modeling of the enantioselectivity of *Pseudomonas cepacia* lipase toward γ-δ-lactones", Journal of Molecular Catalysis B: Enzymatic (2000), vol. 10, pp. 223-231.
Tuomi, W.V., et al., "Molecular Basis for Enantioselectivity of Lipase from *Pseudomonoas cepacia* toward Primary Alcohols. Modeling, Kinetics, and Chemical Modification of Tyr29 to Increase or Decrease Enantioselectivity", J. Org. Chem. (1999), vol. 64, pp. 2638-2647.
Gentner, C., et al., "Primary alcohols in a ring structure: quantifying enantioselectivity of *Pseudomonas cepacia* lipase by an in silico assay", Colloids and Surfaces B: Biointerfaces (2002), vol. 26, pp. 57-66.
Schulz, T., et al., "Stereoselectivity of *Pseudomonas cepacia* lipase toward secondary alcohols: A quantitative model", Protein Science (2000), vol. 9, pp. 1053-1062.
Kim, M.H., et al., "Substitution of Glycine 275 by Glutamate (G275E) in Lipase of *Bacillus stearothermophilus* Affects Its Catalytic Activity and Enantio- and Chain Length Specificity", J. Microbiol. Biotechnol. (2000), vol. 10, No. 5, pp. 764-769.

*Primary Examiner*—Tekchand Saidha
(74) *Attorney, Agent, or Firm*—Connolly Bove Lodge & Hutz LLP

(57) ABSTRACT

The invention relates to a lipase variant which can be prepared by carrying out, on the amino acid sequence of a starting lipase selected from the lipase homologous family I.1 or I.2, at least one amino acid substitution in those positions which correspond to the positions 17, 29, 30, 52, 86, 117, 122, 160, 163, 167, 265, 266, 286, 289 in the prototype lipase sequence SEQ ID NO: 1.

19 Claims, No Drawings

SEQUENCE LISTING

<160> NUMBER OF SEQ ID NOS: 1

<210> SEQ ID NO 1
<211> LENGTH: 319
<212> TYPE: PRT
<213> ORGANISM: Pseudomonas sp.

<400> SEQUENCE: 1

Ala Asp Thr Tyr Ala Ala Thr Arg Tyr Pro Val Ile Leu Val His Gly

-continued

```
 1            5                 10                15
Leu Ala Gly Thr Asp Lys Phe Ala Asn Val Val Asp Tyr Trp Tyr Gly
            20                25                30

Ile Gln Ser Asp Leu Gln Ser His Gly Ala Lys Val Tyr Val Ala Asn
            35                40                45

Leu Ser Gly Phe Gln Ser Asp Asp Gly Pro Asn Gly Arg Gly Glu Gln
50                    55                60

Leu Leu Ala Tyr Val Lys Gln Val Leu Ala Ala Thr Gly Ala Thr Lys
65                    70                75                80

Val Asn Leu Ile Gly His Ser Gln Gly Gly Leu Thr Ser Arg Tyr Val
                85                90                95

Ala Ala Val Ala Pro Gln Leu Val Ala Ser Val Thr Thr Ile Gly Thr
                100               105               110

Pro His Arg Gly Ser Glu Phe Ala Asp Phe Val Gln Asp Val Leu Lys
            115               120               125

Thr Asp Pro Thr Gly Leu Ser Ser Thr Val Ile Ala Ala Phe Val Asn
    130               135               140

Val Phe Gly Thr Leu Val Ser Ser Ser His Asn Thr Asp Gln Asp Ala
145               150               155               160

Leu Ala Ala Leu Arg Thr Leu Thr Thr Ala Gln Thr Ala Thr Tyr Asn
                165               170               175

Arg Asn Phe Pro Ser Ala Gly Leu Gly Ala Pro Gly Ser Cys Gln Thr
            180               185               190

Gly Ala Ala Thr Glu Thr Val Gly Gly Ser Gln His Leu Leu Tyr Ser
            195               200               205

Trp Gly Gly Thr Ala Ile Gln Pro Thr Ser Thr Val Leu Gly Val Thr
    210               215               220

Gly Ala Thr Asp Thr Ser Thr Gly Thr Leu Asp Val Ala Asn Val Thr
225               230               235               240

Asp Pro Ser Thr Leu Ala Leu Leu Ala Thr Gly Ala Val Met Ile Asn
            245               250               255

Arg Ala Ser Gly Gln Asn Asp Gly Leu Val Ser Arg Cys Ser Ser Leu
            260               265               270

Phe Gly Gln Val Ile Ser Thr Ser Tyr His Trp Asn His Leu Asp Glu
            275               280               285

Ile Asn Gln Leu Leu Gly Val Arg Gly Ala Asn Ala Glu Asp Pro Val
    290               295               300

Ala Val Ile Arg Thr His Val Asn Arg Leu Lys Leu Gln Gly Val
305               310               315
```

LIPASE VARIANTS

RELATED APPLICATIONS

This application is a national stage application (under 35 U.S.C. 371) of PCT/EP02/11620 filed Oct. 17, 2002, which claims benefit of German application 101 51 292.9 filed Oct. 22, 2001 and German application 102 05 444.4 filed Feb. 8, 2002.

FIELD OF THE INVENTION

The present invention relates to lipase variants having increased specific activity, processes for the preparation of these lipase variants, and the use of these lipase variants as catalysts in chemical reactions, in particular for the preparation of optically active compounds.

DESCRIPTION OF THE BACKGROUND

The use of the naturally occurring biocatalysts in chemical reactions is limited by numerous factors such as, for example, lack of activity, stability and enantioselectivity. It is therefore desirable to have available novel biocatalysts which have been optimized with respect to these properties.

An industrially important application of lipases is the preparation of optically active amines, alcohols, carboxylic acids and carboxylic acid esters.

EP 0 548 228 discloses optimized lipase variants for use as detergent additives.

SUMMARY OF THE INVENTION

The present invention overcomes the problems and disadvantages associated with current strategies and designs and provides new lipase variants and methods.

One embodiment of the invention is directed to lipase variants comprising an amino acid sequence of a staffing lipase wherein the starting lipase is selected from the group consisting of a of lipases of lipase homologous families I.1 and I.2, wherein the amino acid sequence of said lipase variant contains at least one amino acid substitution at a position that corresponds to position 17, 29, 30, 52, 86, 117, 122, 160, 163, 167, 265, 266, 286, or 289 of SEQ ID NO: 1.

Another embodiment of the invention is directed to formulations containing lipase variants of the invention. Lipase variants of these formulations may be immobilized on a solid carrier material or in cells.

Another embodiment of the invention is directed to nucleic acid sequences and constructs of nucleic acids that encode lipase variants of the invention.

Another embodiment of the invention is directed to host organisms that contain nucleic acids of the invention.

Another embodiment of the invention is directed to processes for production of lipase comprising culturing an organism that expresses a lipase variant of the invention in a culture medium and, if desired, purifying the lipase variant from the culture mixture.

Another embodiment of the invention is directed to processes for enzyme-catalytic conversion or enantioselective conversion of substrates, which comprises reacting the substrates in the presence of the lipase variants of the invention. Preferred substrates are alcohols, amines, amino esters and carboxylic acid esters or racemic alcohols, amines, amino esters and carboxylic acid esters.

DESCRIPTION OF THE INVENTION

The invention is based on the object of making available novel lipase variants having improved properties, e.g. increased specific activity.

Lipase variants have been found which can be prepared by carrying out in the amino acid sequence of a starting lipase, selected from the lipase homologous family I.1 or I.2, at least one amino acid substitution in those positions which correspond to the positions 17, 29, 30, 52, 86, 117, 122, 160, 163, 167, 265, 266, 286, 289 in the sequence of the enzymatically active prototype lipase SEQ ID NO: 1.

The lipase having the amino acid sequence SEQ ID NO. 1 is designated below as a prototype lipase sequence. It is in this case the lipase of the strain *Pseudomonas* spec. DSM 8246.

This strain *Pseudomonas* spec. DSM 8246 is also designated as *Burkholderia plantarii*. The lipases from *Burkholderia plantarii* and *Pseudomonas glumae* have the same sequence (Frenken et al., Cloning of the *Pseudomonas glumae* lipase gene and determination of the active site residues, Appl. Environ. Microbiol. 1992, 58, 3787-3791).

Starting lipases of the lipase homologous families I.1 and I.2 are understood according to the invention as meaning the lipases which can be classified in the homologous classes (table 1) described by Arpigny and Jäger in Biochem. J. 199, 343, 177. Reference is expressly made hereby to this classification. Preferred starting lipases are the lipases from *Pseudomonas aeruginosa*, *Vibrio cholerae*, *Pseudomonas fragi*, *Acinetobacter calcoaceticus*, *Pseudomonas wisconsinensis*, *Pseudomonas fluorescens*, *Pseudomonas vulgaris*, *Burkholderia cepacia*, *Burkholderia glumae*, *Pseudomonas* spec. DSM 8246, *Burkholderia plantarii*, *Chromobacterium viscosum* and *Pseudomonas luteola*.

A particularly preferred starting lipase is the lipase from *Pseudomonas* spec. DSM 8246, whose amino acid sequence is shown in SEQ ID NO: 1.

The amino acid sequences of these preferred lipases are described in Nardini et al., J. Biol. Chem. 2000, 275, 40, page 31223.

It is also possible, however, additionally to use other lipases as starting lipases of the lipase homologous families I.1 and I.2, as long as they satisfy the classification criteria of Arpigny and Jäger.

Lipases and lipase variants are understood according to the invention as meaning lipases, i.e. enzymes which have the enzymatic activity of a lipase. As a rule, such lipase variants are prepared by specific genetic modification of starting lipases. "Evolutive processes", in which a starting molecule is optimized by undirected mutation and selection, are a further possibility of preparing the lipase variants according to the invention.

Amino acid substitution is understood according to the invention as meaning the replacement of an amino acid in the amino acid sequence of the starting lipase by another amino acid, preferably a natural amino acid. Natural amino acids are understood as meaning Ala, Asp, Asn, Cys, Glu, Phe, Gly, His, Ile, Lys, Leu, Met, Pro, Gln, Arg, Ser, Thr, Val, Trp and Tyr.

Since the amino acid sequences of the starting lipases as a rule do not have the same length as the prototype lipase sequence, the positions of the prototype lipase sequence cannot be transferred directly to the starting lipase, but the corresponding homologous positions must be identified. In order to determine these positions, a sequence alignment with the prototype lipase sequence is carried out, such as is described in Nardini et al., J. Biol. Chem. 2000, 275, 40, page 31223 (FIG. 3). Reference is hereby expressly made to this document and the further documents mentioned therein with respect to the sequence alignment and the homologous positions.

As is inferred, for example, from the homology comparison in Nardini et al., J. Biol. Chem. 2000, 275, 40, page 31223, the position $Met^{16}$ of the lipase from *Pseudomonas aeruginosa*, corresponds to the position $Leu^{44}$ in the lipase from *Vibrio cholerae*, to the position $Leu^{17}$ in the lipase from *Pseudomonas Fragi*, to the position $Leu^{49}$ in the lipase from *Acinetobacter calcoaceticus*, to the position $Val^{37}$ in the lipase from *Pseudomonas wisconsinensis*, to the position $Met^{17}$ in the lipase from *Pseudomonas fluorescens*, to the position $Leu^{16}$ in the lipase from *Pseudomonas* vulgaris, to the position $Leu^{17}$ in the lipase from *Burkholderia cepacia*, to the position $Leu^{17}$ in the lipase from *Burkholderia glumae* (identical to SEQ ID NO: 1), to the position $Leu^{17}$ in the lipase from *Chromobacterium viscosum*, and to the position $Leu^{57}$ in the lipase from *Pseudomonas luteola*.

A preferred embodiment of the invention is lipase variants which can be prepared from starting lipases which are selected from the following group:
A lipase from *Pseudomonas aeruginosa*,
B lipase from *Vibrio cholerae*,
C lipase from *Pseudomonas fragi*,
D lipase from *Acinetobacter calcoaceticus*,
E lipase from *Pseudomonas wisconsinensis*,
F lipase from *Pseudomonas fluorescens*,
G lipase from *Pseudomonas vulgaris*,
H lipase from *Burkholderia cepacia*,
I lipase from *Burkholderia glumae*,
J lipase from *Burkholderia plantarii*,
K lipase from *Chromobacterium viscosum*,
L lipase from *Pseudomonas luteola*,
M lipase from *Pseudomonas* spec. DSM 8246

Further preferred embodiments are those lipase variants which are mutated in the following positions compared with the starting lipase:
A lipase from *Pseudomonas aeruginosa*, mutated in position $Met^{17}$,
B lipase from *Vibrio cholerae*, mutated in position $Leu^{44}$,
C lipase from *Pseudomonas Fragi*, mutated in position $Leu^{17}$,
D lipase from *Acinetobacter calcoaceticus*, mutated in position $Leu^{49}$,
E lipase from *Pseudomonas wisconsinensis*, mutated in position $Val^{37}$,
F lipase from *Pseudomonas fluorescens*, mutated in position $Met^{17}$,
G lipase from *Pseudomonas vulgaris*, mutated in position $Leu^{16}$,
H lipase from *Burkholderia cepacia*, mutated in position $Leu^{17}$,
I lipase from *Burkholderia glumae*, mutated in position $Leu^{17}$,
J lipase from *Burkholderia plantarii*, mutated in position $Leu^{17}$,
K lipase from *Chromobacterium viscosum*, mutated in position $Leu^{17}$,
L lipase from *Pseudomonas luteola*, mutated in position $Leu^{57}$,
M lipase from *Pseudomonas* spec. DSM 8246, mutated in position $Leu^{17}$.

Further preferred embodiments are those lipase variants which carry the following substitutions compared with the starting lipase:

A lipase from *Pseudomonas aeruginosa*, where $Met^{16}$ is replaced by $Ala^{16}$, $Thr^{16}$ or $Phe^{16}$,
B lipase from *Vibrio cholerae*, where $Leu^{44}$ is replaced by $Ala^{44}$, $Thr^{44}$ or $Phe^{44}$,
C lipase from *Pseudomonas Fragi*, where $Leu^{17}$ is replaced by $Ala^{17}$, $Thr^{17}$ or $Phe^{17}$,
D lipase from *Acinetobacter calcoaceticus*, where $Leu^{49}$ is replaced by $Ala^{49}$, $Thr^{49}$ or $Phe^{49}$,
E lipase from *Pseudomonas wisconsinensis*, where $Val^{37}$ is replaced by $Ala^{37}$, $Thr^{37}$ or $Phe^{37}$,
F lipase from *Pseudomonas fluorescens*, where $Met^{17}$ is replaced by $Ala^{17}$, $Thr^{17}$ or $Phe^{17}$,
G lipase from *Pseudomonas* vulgaris, where $Leu^{16}$ is replaced by $Ala^{16}$, $Thr^{16}$ or $Phe^{16}$,
H lipase from *Burkholderia cepacia*, where $Leu^{17}$ is replaced by $Ala^{17}$, $Thr^{17}$ or $Phe^{17}$,
I lipase from *Burkholderia glumae*, where $Leu^{17}$ is replaced by $Ala^{17}$, $Thr^{17}$ or $Phe^{17}$,
J lipase from *Burkholderia plantarii*, where $Leu^{17}$ is replaced by $Ala^{17}$, $Thr^{17}$ or $Phe^{17}$,
K lipase from *Chromobacterium viscosum*, where $Leu^{17}$ is replaced by $Ala^{17}$, $Thr^{17}$ or $Phe^{17}$,
L lipase from *Pseudomonas luteola*, where $Leu^{57}$ is replaced by $Ala^{57}$, $Thr^{57}$ or $Phe^{57}$,
M lipase from *Pseudomonas* spec. DSM 8246, where $Leu^{17}$ is replaced by $Ala^{17}$, $Thr^{17}$ or $Phe^{17}$.

Further preferred embodiments are those lipase variants which carry at least one of the following amino acid substitutions compared with the starting lipase from *Pseudomonas* spec DSM 8246:
$Leu^{17}$ replaced by $Ala^{17}$, $Thr^{17}$ or $Phe^{17}$, $Met^{17}$
$Tyr^{29}$ replaced by $Ser^{29}$, $Thr^{29}$, $Phe^{29}$, $Glu^{29}$
$Trp^{30}$ replaced by $His^{30}$, $Phe^{30}$
$Phe^{52}$ replaced by $Ser^{52}$, $Thr^{52}$ or $Tyr^{52}$, $Leu^{52}$
$His^{86}$ replaced by $Trp^{86}$, $Thr^{86}$, $Ser^{86}$
$Ser^{117}$ replaced by $Ala^{117}$, $Thr^{117}$, $Met^{117}$
$Phe^{122}$ replaced by $Leu^{122}$
$Ala^{160}$ replaced by $Phe^{160}$, $Leu^{160}$, $Ile^{160}$
$Ala^{163}$-replaced by $Phe^{163}$, $Leu^{163}$, $Ile^{163}$
$Leu^{167}$ replaced by $Ala^{167}$, $Val^{167}$, $Ser^{167}$, $Thr^{167}$
$Leu^{265}$ replaced by $Ala^{265}$, $Val^{267}$ or $Met^{265}$, $Ser^{265}$, $Thr^{265}$
$Val^{266}$ replaced by $Ala^{266}$, $Leu^{266}$, $Met^{266}$, $Ser^{266}$, $Lys^{266}$
$Leu^{286}$ replaced by $Ala^{286}$, $Met^{286}$, $Val^{286}$ or $Ile^{286}$, $Ser^{286}$
$Ile^{289}$ replaced by $Ala^{289}$, $Val^{289}$ or $Leu^{289}$.

A particularly preferred embodiment is a lipase variant which carries two of the following amino acid substitutions compared with the starting lipase from *Pseudomonas* spec DSM 8246:
$Leu^{17}$ replaced by $Ala^{17}$, $Thr^{17}$, $Phe^{17}$, $Met^{17}$
$Phe^{52}$ replaced by $Leu^{52}$, $Ser^{52}$, $Thr^{52}$ or $Tyr^{52}$.

A further subject of the invention are nucleic acid sequences which encode the lipase variants according to the invention described above. Suitable nucleic acid sequences are obtainable by back-translation of the polypeptide sequence according to the genetic code.

Preferably, the codons used for this are those frequently used in accordance with the codon usage specific to the organism. The codon usage can easily be determined with the aid of computer analysis of other, known genes of the organism concerned.

Should the lipase variant be expressed, for example, in a bacterium, it is frequently advantageous to use the codon usage of the bacterium in the back-translation.

A further subject of the invention is nucleic acid constructs which contain the nucleic acid sequences according to the invention. These nucleic acid constructs preferably carry, in addition to the nucleic acid sequences, also regulatory sequences which are advantageous, for example, for expression, replication or recombination.

A further subject of the invention are host organisms which can be transformed using these nucleic acid constructs. Suitable host organisms are unicellular or multicellular organisms, microorganisms being preferred as host organisms.

A further subject of the invention is processes for the preparation of lipase variants by culturing host organisms, which have been transformed using a nucleic acid-sequence coding for the lipase variants, under those conditions which allow the production of the lipase variants in these host organisms. Subsequently, when the concentration of the lipase variant in the culture medium has reached the desired level, the lipase variant can be isolated from the culture medium. Depending on the desired intended use of the lipase, this can also be purified using customary processes of protein chemistry such as precipitation and chromatography. For some intended uses, however, the entire host organism can also be used, if appropriate after prior destruction.

The invention furthermore relates to lipase formulations comprising at least one of the lipase variants according to the invention.

The lipase variants can be used in this formulation in isolated form, immobilized on a solid carrier material or in cells. Such lipase formulations can contain, in addition to the lipase variant, also further stabilizers, detergents and enzyme substrates.

Methods for the immobilization of lipases are described, for example, in WO 00/05354, EP 1069183.

Preferably, the lipase variants are used in immobilized form.

The invention furthermore relates to a process for the enzyme-catalytic conversion or enantioselective conversion of substrates by reacting the substrates in the presence of the lipase according to the invention.

The lipase variants according to the invention can accordingly be used as catalysts in chemical reactions. The lipase variants according to the invention can be employed in a multiplicity of chemical reactions.

The catalytic properties of the lipase variants according to the invention are measured using reference reactions. Thus, good higher specific activities compared with the starting lipases can also be determined:

The determination of the specific activity of a lipase variant is carried out according to the invention in the following reference reaction, in which the lipase or lipase variant catalyzes the reaction of racemic trans-methoxycyclohexanol with vinyl laurate to give lauric acid 1R,2R-2-methoxycyclohexyl ester and 1S,2S-methoxycyclohexanol.

The specific activity is determined in this reference reaction under the following conditions:

The reference reaction is carried out in microtiter plates having 96 cavities. The microtiter plate contains, per cavity A the lipase-containing lyophyllisate of 150 µl of culture supernatant of cultures of natural or recombinant organisms which express a lipase or B the corresponding, firmly prespecified amount of isolated lipase.

For separation of the racemates, racemic trans-methoxycyclohexanol and vinyl laurate are employed in the molar ratio 1:0.65 [i.e. per plate 10 g of methoxycyclohexanol and 11.3 g of vinyl laurate]. 200 µl of this mixture are pipetted into each well.

Each plate is sealed using a 'plate sealer', closed with a lid and incubated for 96 h at room temperature in a revolving shaker at 150 rpm. 100 µl per cavity in each case are then removed, treated with ethyl acetate and analyzed by gas chromatography.

The amount of methoxycyclohexyl laurate formed is measured relative to the amount of the lipase employed (case B) or relative to the optical density of the cell suspensions in the cavities of the microtiter plates (case A).

In case A, it must be guaranteed that all further measurement parameters and other parameters, such as, for example, induced and constitutive expression, are identical in the organisms which express the respective lipase.

A larger amount of methoxycyclohexyl laurate measured according to this method per amount of lipase means a higher specific activity.

Enzyme-catalytic conversions are understood as meaning chemical reactions of substrates which lipases can catalyze. The following reactions may be mentioned by way of example:

acylation or enantioselective acylation of alcohols,
acylation or enantioselective acylation of amines,
acylation or enantioselective acylation of amino esters, such as, for example, amino acid esters,
hydrolysis or enantioselective hydrolysis of carboxylic acid esters,
acylation or enantioselective acylation of cyanohydrins,
hydrolysis or enantioselective hydrolysis of cyanohydrin esters,
asymmetrisization of meso-diols or
asymmetrisization of meso-diesters by hydrolysis.

Preferred processes are processes for the
acylation or enantioselective acylation of alcohols,
acylation or enantioselective acylation of amines,
acylation or enantioselective acylation of amino esters, such as, for example, amino acid esters or a process for the hydrolysis or enantioselective hydrolysis of carboxylic acid esters.

The process for the enzyme-catalytic conversion or enantioselective conversion of substrates comprises reacting the substrates in the presence of the lipase variants according to the invention.

Depending on whether the type of reaction necessitates it, further reagents are preferably added here. Thus, an acylation, for example, necessitates the addition of an acylating agent, while hydrolysis, for example, needs no further addition of reagents.

Substrate is understood as meaning a chemical compound which can be reacted by enzyme catalysis, i.e. chemically modified, by lipases. In enantioselective conversions, stereoisomer mixtures of which only one stereoisomer is reacted are likewise substrates.

By way of example, alcohols, amines, amino esters, amides, carboxylic acid esters, thioesters, thiols, cyanohydrins, cyanohydrin esters and meso-diols and their stereoisomer mixtures may be mentioned as substrates. Preferred substrates are alcohols, amines, amino esters and carboxylic acid esters or racemic alcohols, amines, amino esters and carboxylic acid esters.

The process is preferably carried out in solution, in the case of liquid substrates with or without solvent. Solvents which can be used are, for example, water, organic solvents or alternatively aqueous/organic two-phase mixtures.

Preferably, the organic solvents used are dioxane, THF, diethyl ether, methyl t-butyl ether (MTBE), toluene or heptane. The aqueous/organic two-phase mixture employed is preferably a water/MTBE mixture in any desired ratio.

When carrying out the process in solution, the substrate concentration is not critical, but is preferably between 0.5% by weight and 50% by weight based on the solution; 20 to 30% by weight is particularly preferred. The temperature when carrying out the process is likewise not critical, but is restricted upwardly by the temperature stability of the enzyme. Preferably, the process is carried out at 0° C. to 60° C.; 15° C. to 40° C. is particularly preferred.

The process can be carried out continuously or batchwise. For carrying out the process continuously, a liquid mobile phase is passed in a manner known per se, for example, into a reactor through a packed bed of immobilized lipase variant. The mobile phase can be either a solution of substrate (and reagents) or the liquid substrate (and reagents) without solvent. The flow rate is not critical and depends on process technology viewpoints such as the height, diameter and particle size of the packed bed, and on the design of the reactor.

Reactors used for the continuous process are preferably the reactors customary for continuous, heterogeneous catalytic processes (fluid/solid reactions) (J. Hagen, Chemische Reaktionstechnik, VCH, Weinheim 1992, pp. 165-169). By way of example, fluidized bed reactors and fixed bed reactors, such as a tubular reactor, column reactor, chamber reactor, shelf reactor, tube bundle reactor and catalytic furnace, may be mentioned.

In the batchwise process procedure, the immobilized lipase variants are suspended in a solution of substrate (and reagents) or in liquid substrates (and reagents) with or without solvent in a reactor in a manner known per se and the suspension is thoroughly mixed. Reactors used for the batchwise process are preferably the reactors having a shaking, mixing or stirring device customary for batchwise, heterogeneous catalytic processes (fluid/solid reactions). By way of example, the stirred vessel and designs derived therefrom and also reaction vessels having a shaking device may be mentioned.

After completion of the reaction (achievement of the thermodynamic equilibrium), the immobilized lipase variant is isolated, for example by decanting, centrifuging off or filtering off and washing, and used in further reactions.

In a preferred embodiment of the process, substrates which contain acylatable functional groups such as, for example, hydroxyl or amino groups, such as alcohols, amines or amino acid esters, are acylated or enantioselectively acylated in the presence of the immobilized lipase as catalyst and an acylating agent.

This enzyme-catalytic conversion is preferably carried out in an organic solvent such as, for example, dioxane, THF, diethyl ether, methyl t-butyl ether (MTBE), toluene or heptane.

A process for the acylation or enantioselective acylation of alcohols, amines or amino acid esters or racemic alcohols, amines or amino acid esters in the presence of an acylating agent and the lipase variant of SEQ. ID. NO.1 is particularly preferred.

There is virtually no restriction with respect to the alcohols, amines and amino acid esters. Thus it is possible to use mono- and polyhydric alcohols, such as, for example
1-phenylethanol,
optionally substituted 2-chloro-1-phenylethanol,
pent-3-yn-2-ol,
1-butyn-3-ol,
2-hydroxy-4-phenylbutyric acid esters,
a-methyl-(1,3)-benzodioxole-5-ethanol,
2-propanol-1-(1,3-benzodioxol-4-yl),
trans-2-methoxycyclohexanol,
2-methoxy-2-phenylethanol,
cis-2-methyl-4-hydroxypyran or
trans-2-methyl-4-hydroxypyran
or their stereoisomer mixtures,
mono- and polyhydric amines or their stereoisomer mixtures or
α, β or γ-amino acid esters such as, for example, the optionally halogen-substituted $C_1$-$C_4$-alkyl, alkylaryl, aryl, $C_2$-$C_6$-alkenyl or $C_2$-$C_6$-alkynyl esters of the natural amino acids or their stereoisomer mixtures.

Optionally substituted 2-chloro-1-phenylethanol is understood as meaning in particular 2-chloro-1-phenylethanol and substituted 2-chloro-1-phenylethanol. Preferred substituted 2-chloro-1-phenylethanols are alcohols of the formula III

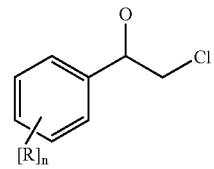

where
n is 1 to 3 and
R, independently of one another, are halogen, in particular F or Cl, $C_1$-$C_4$-alkoxy, in particular methoxy, and $NO_2$.

A particularly preferred substituted 2-chloro-1-phenylethanol is 2-chloro-1-(m-chlorophenyl)ethanol.

The substrate preferably used is racemic trans-2-methoxycyclohexanol.

Acylating agents are understood as meaning organic compounds which can function as acyl transfer agents in the presence of lipases in solution. The following may be mentioned by way of example:
aliphatic, araliphatic or aromatic carboxylic acids which are optionally substituted by halogen, such as Cl, Br, I, F (acylation), such as
$C_1$-$C_6$-alkanecarboxylic acids, e.g. formic acid, acetic acid, propionic acid, butyric acid or
such as araliphatic or aromatic carboxylic acids, e.g. benzoic acid, 3-phenylpropionic acid or
the corresponding carboxylic acid esters (transesterification), such as, for example,
3-phenylpropionic acid esters or alkyl acetates, such as, for example, ethyl acetate.

Preferred carboxylic acid esters as acylating agents are vinyl esters of the formula I

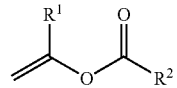

in which
$R^1$ is hydrogen or a $C_1$-$C_4$-alkyl group, preferably a methyl group and
$R^2$ is hydrogen, $C_1$-$C_{18}$-alkyl optionally substituted by halogen, phenyl or ($C_1$-$C_3$-)alkoxy-($C_1$-$C_4$)-alkyl.

Preferred vinyl esters of the formula I are vinyl formate, vinyl acetate, vinyl propionate, vinyl butyrate and vinyl laurate.

Acylating agents are furthermore aliphatic, cycloaliphatic, araliphatic or aromatic carboxylic anhydrides and mixed carboxylic anhydrides (acylation) such as acetic anhydride, succinic anhydride (SA), butyric anhydride, 2-ethylhexanoic anhydride or methylsuccinic anhydride. In the case of the use of succinic anhydride (SA) or other poorly soluble anhydrides as acylating agents, propylene carbonate can be particularly advantageously admixed in order to bring the SA into solution. This is especially of importance with respect to a continuous process.

A particularly preferred acylating agent is vinyl laurate.

In a further preferred embodiment of the process, the carboxylic acid esters are hydrolyzed or enantioselectively hydrolyzed in the presence of the lipase variants or lipase formulations according to the invention.

In this case, no further reagents have to be added; nevertheless, the presence of water is necessary. Preferably, the hydrolysis of carboxylic acid esters is carried out by addition of water using a preferably two-phase system such as, for example, water/MTBE in the presence of the lipase variants or lipase formulations according to the invention.

There is virtually no restriction with respect to the carboxylic acid esters. Thus it is possible, for example, compounds of the formula II or their stereoisomer mixtures

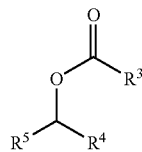

II where
$R^3$, $R^4$ and $R^5$ independently of one another are hydrogen, halogen, such as, for example, F, Cl, Br or I,
a branched or unbranched, optionally substituted
$C_1$-$C_8$-alkyl radical, such as, for example, optionally substituted methyl, ethyl, propyl, 1-methylethyl, butyl, 1-methylpropyl, 2-methylpropyl, 1,1-dimethylethyl, pentyl, 1-methylbutyl, 2-methylbutyl, 1,2-dimethylpropyl, 1,1-dimethylpropyl, 2,2-dimethylpropyl, 1-ethylpropyl, hexyl, 1-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, heptyl or octyl,
$C_6$-alkenyl radical, such as, for example, optionally substituted 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl or 1-ethyl-2-methyl-2-propenyl,
$C_3$-$C_6$-alkynyl radical, such as, for example, optionally substituted 2-propynyl, 2-butynyl, 3-butynyl, 1-methyl-2-propynyl, 2-pentynyl, 3-pentynyl, 4-pentynyl, 1-methyl-3-butynyl, 2-methyl-3-butynyl, 1-methyl-2-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 3-methyl-2-pentynyl, 4-methyl-2-pentynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl or 1-ethyl-1-methyl-2-propynyl
or $C_3$-$C_8$-cycloalkyl radical, such as, for example, optionally substituted cyclopropyl, cyclobutyl, cyclopentyl, cyclohexyl and cycloheptyl, cyclooctyl,
an optionally substituted
aryl radical, such as, for example, optionally substituted phenyl, 1-naphthyl or 2-naphthyl,
arylalkyl radical, such as, for example, optionally substituted benzyl,
heteroaryl radical, such as, for example, optionally substituted 2-pyridyl, 3-pyridyl, 4-pyridyl, 2-furyl, 3-furyl, 2-pyrrolyl, 3-pyrrolyl, 2-thienyl, 3-thienyl, 2-thiazolyl, 4-thiazolyl, 5-thiazolyl, 2-oxazolyl, 4-oxazolyl, 5-oxazolyl, 2-pyrimidyl, 4-pyrimidyl, 5-pyrimidyl, 6-pyrimidyl, 3-pyrazolyl, 4-pyrazolyl, 5-pyrazolyl, 3-isothiazolyl, 4-isothiazolyl, 5-isothiazolyl, 2-imidazolyl, 4-imidazolyl, 5-imidazolyl, 3-pyridazinyl, 4-pyridazinyl, 5-pyridazinyl or 6-pyridazinyl, preferably 2-pyridyl, 3-pyridyl, 4-pyridyl, 2-furyl, 3-furyl, 2-thienyl, 3-thienyl, 2-thiazolyl, 4-thiazolyl or 5-thiazolyl,
or heterocycloalkyl or -alkenyl radical.

Possible mono to triple substituents of the $C_1$-$C_8$-alkyl, $C_2$-$C_6$-alkenyl, $C_2$-$C_6$-alkynyl, $C_3$-$C_8$-cycloalkyl, aryl, arylalkyl, heteroaryl, heterocycloalkyl or -alkenyl radicals are, for example, halogen, nitro, amino, hydroxyl or cyano groups, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, hetaryl, aryl radicals or the radical —O—CO—$C_1$-$C_4$-alkyl.

Preferred carboxylic acid esters are, for example,
1-butyn-3-ol acetate,
1-butyn-3-ol butyrate,
1-phenylethyl acetate or
2-acetoxy-4-phenylbutyric acid esters.

The process for the enantioselective enzyme-catalytic conversion of substrates using the lipase variants or lipase formulations according to the invention can be used for the separation of stereoisomers and in particular for the separation of enantiomers or diastereomers from a stereoisomer mixture of the substrate. Particularly preferably, it is used for the separation of enantiomers or diastereomers from racemic substrates and thus for the preparation of optically active compounds from the respective racemic mixtures.

Owing to the enantioselective substrate specificity of the lipase variants or lipase formulations according to the invention, only one enantiomer, for example, of the racemic substrate is converted; the other enantiomer does not react. The resulting products can be easily separated in a manner known per se by chemical, physical and mechanical separation methods.

Crystallization, precipitation, extraction in two-phase solvent systems, chromatographic separation processes, such as HPLC, GC or column chromatography on silica gel or thermal separation processes such as distillation may be mentioned by way of example.

Accordingly, the present invention furthermore relates to a process for the preparation of optically active compounds, which comprises reacting stereoisomer mixtures or racemates of substrates, which can be reacted by means of enzyme catalysis by lipases, enantioselectively in the presence of the lipase variants according to the invention and then resolving the mixtures.

Using the process according to the invention, preferably the optically active compounds can be prepared which can be reacted as a stereoisomer mixture as substrates of lipases, or at least one stereoisomer of their stereoisomer mixture can be reacted as a substrate of lipases.

A process for the enantioselective acylation of alcohols, amines or amino acid esters is preferably used for the separation of racemic alcohols, amines or amino acid esters and thus for the preparation of optically active alcohols, amines or amino acid esters.

A process for the enantioselective hydrolysis of carboxylic acid esters is preferably used for the separation of racemic carboxylic acid esters and thus for the preparation of optically active carboxylic acid esters.

The lipase variants or lipase formulations according to the invention have the advantage that they have an increased specific activity together with constant enantioselectivity.

The examples below illustrate the invention:

General Experimental Conditions

In all cases in which no detailed description of the experiments takes place, molecular biology methods were used which are known and are described, for example, in Current Protocols of Molecular Biology, 1999, John Wiley & Sons.

Bacterial strains used:
*Escherichia coli* XL1-Blue (Stratagene)
*Escherichia coli* XJS5037 (pRK2013) (Proc. Natl. Acad. Sci., 1979, 1648-1652) *Pseudomonas* spec. DSM 8246

Plasmids used:
pBluescriptIIKS (Stratagene),
pBP1500: Derivative of pML131 (Gene, 1990, 89:37-46) with a 2.6 kBp DNA fragment which comprises the lipase operon from *Pseudomonas* spec. DSM 8246. pBP1500 codes for an enzymatically inactive lipase (lipA_),
pBP1520: Derivative of pML131 (Gene, 1990, 89:37-46) with a 2.6 kBp DNA fragment which comprises the lipase operon from *Pseudomonas* spec. DSM 8246. pBP1520 codes for an enzymatically active lipase (lipA),
pBP2112: Derivative of pML131 (Gene, 1990, 89:37-46) with a 2.6 kBp DNA fragment which-comprises the lipase operon from *Pseudomonas* spec. DSM 8246 and which comprises the mutation for the production of the lipase variant LipA L17A.

EXAMPLE 1

Preparation of a Lipase Variant Having Increased Specific Enzyme Activity

A) Culturing of the Bacteria

The recombinant strains of *Escherichia coli* were cultured either on solid LB agar or in LB medium at 37° C. in a rotary shaker at 200 rpm for 16 h. The medium contained the antibiotics necessary for election *Pseudomonas* spec. DSM 8246 and the recombinant derivatives of this strain were either incubated on solid FG agar or in FP medium at 30° C. in a rotary shaker at 200 rpm for 24 h or in $(NH_4)_2SO_4$ 6 g/l, $CaCl_2$ 0.02 g/l, $MgSO_4 \times 7H_2I$ 1 g/l, $KH_2PO_4$ 3.5 g/l, $K_2HPO_4$ 3.5 g/l, yeast extract 5 g/l, glucose 5 g/l, trace salt solution 10 ml/l at 30° C. in a rotary shaker at 150 rpm for 24 h. The medium contained the antibiotics necessary for selection. As incubation vessels, petri dishes, culture tubes or microtiter plates were used.

The following antibiotics (selection) were used: tetracycline 10 μl/ml (XL1-Blue), ampicillin 100 μg/ml (pBluescriptIIKS), gentamicin 10 μg/ml (pBP plasmids in *E. coli*), gentamicin 45 μg/ml (pBP plasmids in *Pseudomonas* spec. DSM 8246), chloramphenicol 20 μg/ml (*Pseudomonas* spec. DSM 8246), kanamycin 25 μg/ml (*Escherichia coli* XJS5037 (pRK2013) or *Pseudomonas* spec. DSM 8246)

B) Mutagenesis

The mutant L17A of lipA from *Pseudomonas* spec. DSM 8246 was produced by site-directed mutagenesis using the overlap extension PCR method (Recombinant PCR, 1990, 177-183, Academic Press, San Diego).

Chromosomal DNA from *Pseudomanas* spec. DSM 8246 was used as matrix DNA. The primers employed were:

```
                                        (SEQ ID NO: 2)
MAT16    5'-GATCGACGTAAGCTTTAACGATGGAGAT-3'

(SEQ ID NO: 3)
MAT109   5'-CGGTGCCCGCGGCGCCGTGGACGAGGATCACCG-3'

(SEQ ID NO: 4)
MAT108   5'-CGTCCACGGCGCCGCGGGCACCGACAAGTTCGC-3'

(SEQ ID NO: 5)
MAT19    5'-CATCGGGCGAGCTCCCAGCCCGCCGCG-3'
```

In the first PCR step, a subfragment of lipA was produced using MAT16 and MAT109 and a further subfragment of lipA was produced using MAT108 and MAT19. The subfragments were separated in an agarose gel and purified using the GFX kit (Pharmacia). The fragment lipA* which codes for the lipase variant L17A was produced from the purified fragments in the second PCR step using MAT16 and MAT19.

The PCR was carried out according to the procedure of the manufacturer using the GC-rich kit (Pharmacia) with the following temperature profile: (1) 95° C.-3 min, (2) 95° C.-30 s, (3) 40° C.-30 s, (4) 72° C.-30 s, (5) 95° C.-30 s, (6) 60° C.-30 s, (7) 72° C. 30 s, (8) 72° C.-10 min; steps (2)-(4) with 5 cycles; then steps (5)-(7) 15 cycles.

The fragment lipA* and the vector pBluescriptIIKS were cleaved using HindIII and SacI, separated in an agarose gel, purified using the GFX kit and ligated. The batch was then transformed into *E. coli*. The recombinant plasmid was purified and sequenced in order to detect the mutation. Except for the mutation L17A, no further mutations were detected in the DNA.

C) Cloning

The vector pBP1500 and the recombinant pBluescript derivative with lipA* was cleaved using HindIII and SacI and ligated. The resultant recombinant plasmid was designated pBP2112. pBP2112 was transformed into *E. coli* XL1-Blue. pBP2112 was then transferred to *Pseudomonas* spec. DSM 8246 by conjugation of *E. coli* XL1-Blue with the aid of the helper strain *E. coli* XJS5037 (pRK2013). The recombinant strain was designated *Pseudomonas* spec. DSM 8246 (pBP2112).

D) Enzyme Production and Work-up

*Pseudomonas* spec. DSM 8246 (pBP2112) was incubated at 30° C. for 24 h in 96-cavity microtiter plates each containing 250 μl of medium per cavity on a rotary shaker at 150 rpm. As a control, *Pseudomonas* spec. DSM 8246 (pBP1520) was cultured. This strain carries the lipA gene of Pseudomonas spec. DSH 8246 in plasmid-coded form (comparison example). The following medium was employed for the culture of the bacteria: $(NH_4)_2SO_4$ 6 g/l, $CaCl_2$ 0.02 g/l, $MgSO_4 \times 7H_2O$ 1 g/l, $KH_2PO_4$ 3.5 g/l, $K_2HPO_4$ 3.5 g/l, yeast extract 5 g/l, glucose 5 g/l, trace salt solution 10 ml/l, kanamycin 25 µl/ml, gentamicin 45 µg/ml. After the culture, the microtiter plates were centrifuged. The culture supernatants were then transferred to a polypropylene microtiter plate, frozen at −80° C. for 16 h and then freeze-dried for 48 h.

The chromosomal copy of the lipase gene is not expressed under the culturing conditions. The comparison example therefore also carries the natural lipase in plasmid-coded form.

E) Resolution and Analysis

The resolution of rac-trans-2-methoxycyclohexanol was carried out in the microtiter plates containing the freeze-dried supernatants. For the resolution, methoxycyclohexanol and vinyl laurate were employed in a molar ratio of 1:0.65 [i.e. 10 g of methoxycyclohexanol and 11.3 g of vinyl laurate per plate]. 200 µl of this mixture were pipetted into each cavity. Each plate was sealed using a 'plate sealer', closed with a cover and incubated for 96 h at room temperature in a rotary shaker at 150 rpm.

100 ml per cavity were then removed, treated with ethyl acetate and analyzed by gas chromatography.

Table 1 contains the measured amounts of methoxycyclohexanyl laurate formed in % by weight.

TABLE 1

| Example 1E Amount of methoxycyclohexanyl laurate formed in [% by weight] using the lipase variant LipA L17A from Pseudomonas spec. DSM 8246 (pBP2112) | Comparison example Amount of methoxycyclohexanyl laurate formed in [% by weight] using the lipase from Pseudomonas spec. DSM 8246 (pBP1520) | Media blank |
|---|---|---|
| 14.9 | 2.6 | 0.02 |
| 18.6 | 1.0 | 0.02 |
| 21.2 | 2.5 | 0.02 |
| 18.1 | 2.7 | 0.02 |
| 16.8 | 2.2 | 0.03 |
| 14.0 | 1.7 | 0.02 |
| 15.1 | 1.8 | 0.03 |
| 10.3 | 0.8 | 0.02 |
| Mean = 16.1 | Mean = 1.9 | Mean = 0.02 |

In comparison with the natural enzyme, the lipase variant LipA L17A showed an activity which was higher by the factor 8.5 in the resolution of methoxycyclohexanol.

The specific enzyme activity is in this case defined as the amount of methoxycyclohexanyl laurate formed in [% by weight] divided by optical density of the bacterial suspension at $OD_{660\,nm}$. The amount of active enzyme formed correlates in a range of an optical density of $OD^{660\,nm} \approx 0.0$ to 0.7+/−0.2 linearly with the turbidity of the bacterial suspension.

The following values resulted here for the specific activity:

TABLE 2

| Specific activity of the lipase variant LipA L17A from Pseudomonas spec. DSM 8246 (pBP2112) in the reaction according to example 1E [in % by weight] | Comparison example: Specific activity of the lipase from Pseudomonas spec. DSM 8246 (pBP1520) in the reaction according to example 1E [in % by weight] | Media blank |
|---|---|---|
| 16.4 | 3.1 | 0.5 |
| 20.2 | 1.2 | 0.5 |
| 22.1 | 3.0 | 0.5 |
| 20.3 | 3.4 | 0.5 |
| 19.1 | 2.8 | 0.8 |
| 14.4 | 2.2 | 0.5 |
| 17.4 | 2.4 | 0.8 |
| 10.8 | 1.0 | 0.5 |
| Mean = 17.6 | Mean = 2.4 | Mean = 0.6 |

In comparison with the natural enzyme, the lipase variant LipA L17A showed a specific enzyme activity which was higher by the factor 7.3 in the resolution of methoxycyclohexanol.

We claim:

1. A lipase variant comprising an amino acid sequence of a starting lipase that has been substituted, wherein the starting lipase is selected from the group consisting of lipases of homologous families I.1 and I.2, wherein the substitution is at least one amino acid substitution at a position that corresponds to position 17, 29, 30, 52, 86, 117, 122, 160, 163, 167, 265, 266, 286, or 289 of SEQ ID NO: 1, and wherein the variant has lipase activity.

2. The lipase variant of claim 1, wherein the starting lipase is a lipase from an organism selected from the group of organisms consisting of *Pseudomonas aeruginosa, Vibrio cholerae, Pseudomonas fragi, Acinetobacter calcoaceticus, Pseudomonas wisconsinensis, Pseudomonas fluorescens, Pseudomonas vulgaris, Burkholderia cepacia, Burkholderia glumae, Burkholderia plantarii, Chromobacterium viscosum, Pseudomonas luteola*, and *Pseudomonas* spec. DSM 8246.

3. The lipase variant of claim 1 selected from the group consisting of:
   a lipase from *Pseudomonas aeruginosa*, with a substitution at position Met[16];
   a lipase from *Vibrio cholerae*, with a substitution at position Leu[44];
   a lipase from *Pseudomonas Fragi*, with a substitution at position Leu[7];
   a lipase from *Acinetobacter calcoaceticus*, with a substitution at position Leu[49];
   a lipase from *Pseudomonas wisconsinensis*, with a substitution at position Val[37];

a lipase from *Pseudomonas fluorescens*, with a substitution at position Met$^{17}$;
a lipase from *Pseudomonas vulgaris*, with a substitution at position Leu$^{16}$;
a lipase from *Burkholderia cepacia*, with a substitution at position Leu$^{17}$;
a lipase from *Burkholderia glumae*, with a substitution at position Leu$^{17}$;
a lipase from *Burkholderia plantarii*, with a substitution at position Leu$^{17}$;
a lipase from *Chromobacterium viscosum*, with a substitution at position Leu$^{17}$;
a lipase from *Pseudomonas luteola*, with a substitution at position Leu$^{57}$; and
a lipase from *Pseudomonas* spec. DSM 8246, with a substitution at position Leu$^{17}$.

4. The lipase variant of claim 1 selected from the group consisting of:
a lipase from *Pseudomonas aeruginosa*, wherein Met$^{16}$ is substituted with Ala$^{16}$, Thr$^{16}$ or Phe$^{16}$;
a lipase from *Vibrio cholerae*, wherein Leu$^{44}$ is substituted with Ala$^{44}$, Thr$^{44}$ or Phe$^{44}$;
a lipase from *Pseudomonas Fragi*, wherein Leu$^{17}$ is substituted with Ala$^{17}$, Thr$^{17}$ or Phe$^{17}$;
a lipase from *Acinetobacter calcoaceticus*, wherein Leu$^{49}$ is substituted with Ala$^{49}$, Thr$^{49}$ or Phe$^{49}$;
a lipase from *Pseudomonas wisconsinensis*, wherein Val$^{37}$ is substituted with Ala$^{37}$, Thr$^{37}$ or Phe$^{37}$;
a lipase from *Pseudomonas fluorescens*, wherein Met$^{17}$ is substituted with Ala$^{17}$, Thr$^{17}$ or Phe$^{17}$;
a lipase from *Pseudomonas vulgaris*, wherein Leu$^{16}$ is substituted with Ala$^{16}$, Thr$^{16}$ or Phe$^{16}$;
a lipase from *Burkholderia cepacia*, wherein Leu$^{17}$ is substituted with Ala$^{17}$, Thr$^{17}$ or Phe$^{17}$;
a lipase from *Burkholderia glumae*, wherein Leu$^{17}$ is substituted with Ala$^{17}$, Thr$^{17}$ or Phe$^{17}$;
a lipase from *Burkholderia plantarii*, wherein Leu$^{17}$ is substituted with Ala$^{17}$, Thr$^{17}$ or Phe$^{17}$;
a lipase from *Chromobacterium viscosum*, wherein Leu$^{17}$ is substituted with Ala$^{17}$, Thr$^{17}$ or Phe$^{17}$;
a lipase from *Pseudomonas luteola*, wherein Leu$^{57}$ is substituted with Ala$^{57}$, Thr$^{57}$ or Phe$^{57}$;
a lipase from *Pseudomonas* spec. DSM8246, wherein Leu$^{17}$ is substituted with Ala$^{17}$, Thr$^{17}$ or Phe$^{17}$.

5. The lipase variant of claim 1, wherein the at least one amino acid substitution comprises two substitutions that correspond to the positions 17 and 52 of SEQ ID NO: 1.

6. The lipase variant of claim 1, wherein the starting lipase is from *Pseudomonas* spec. DSM 8246 and the at least one substitution is selected from the group of substitutions consisting of:
Leu$^{17}$ replaced by Ala$^{17}$, Thr$^{17}$, Phe$^{17}$, or Met$^{17}$;
Tyr$^{29}$ replaced by Ser$^{29}$, Thr$^{29}$, Phe$^{29}$, or Glu$^{29}$;
Trp$^{30}$ replaced by His$^{30}$ or Phe$^{30}$;
Phe$^{52}$ replaced by Ser$^{52}$, Thr$^{52}$, Tyr$^{52}$ or Leu$^{52}$;
His$^{86}$ replaced by Trp$^{86}$, Thr$^{86}$ or Ser$^{86}$;
Ser$^{117}$ replaced by Ala$^{117}$, Thr$^{117}$ or Met$^{117}$;
Phe$^{122}$ replaced by Leu$^{122}$;
Ala$^{160}$ replaced by Phe$^{160}$, Leu$^{160}$ or Ile$^{160}$;
Ala$^{163}$ replaced by Phe$^{163}$, Leu$^{163}$ or Ile$^{163}$;
Leu$^{167}$ replaced by Ala$^{167}$, Val$^{167}$, Ser$^{167}$ or Thr$^{167}$;
Leu$^{265}$ replaced by Ala$^{265}$, Val$^{267}$, Met$^{265}$, Ser$^{265}$ or Thr$^{265}$;
Val$^{266}$ replaced by Ala$^{266}$, Leu$^{266}$, Met$^{266}$, Ser$^{266}$ or Lys$^{266}$;
Leu$^{286}$ replaced by Ala$^{286}$, Met$^{286}$, Val$^{286}$, Ile$^{286}$ or Ser$^{286}$; and
Ile$^{289}$ replaced by Ala$^{289}$, Val$^{289}$ or Leu$^{289}$.

7. A nucleic acid sequence that encodes the lipase variant of claim 1.

8. A nucleic acid construct comprising the nucleic acid sequence of claim 7.

9. An isolated host cell transformed with the nucleic acid construct of claim 8.

10. A process for production of lipase comprising culturing an organism that expresses the lipase variant of claim 1 in a culture medium.

11. A lipase formulation comprising the lipase variant of claim 1 and a stabilizer, detergent, enzyme substrate, or a combination thereof.

12. A lipase formulation comprising the lipase variant of claim 1 that is immobilized on a solid carrier material or is in cells.

13. A process for enzyme-catalytic conversion or enantioselective conversion of substrates, which comprises reacting the substrates in the presence of the lipase variant of claim 1.

14. The process of claim 13, wherein the substrates comprise alcohols, or amine or amino acid esters that are acylated in the presence of an acylating agent.

15. The process of claim 13, wherein the substrates comprise carboxylic acid esters that are hydrolyzed.

16. A process for preparation of optically active compounds, which comprises reacting stereo isomer mixtures or racemates of substrates in an enzyme-catalyzed manner enantioselectively in the presence of the lipase variant of claim 1; and then resolving the mixtures.

17. The process of claim 16, wherein the substrates comprise alcohols, amines or amino acid esters that are enantioselectively acylated in the presence of an acylating agent.

18. The process of claim 10, further comprising recovering said lipase variant from the culture medium.

19. A lipase variant consisting of an amino acid sequence of a starting lipase that has been substituted, wherein the starting lipase is selected from the group consisting of lipases of homologous families I.1 and I.2, wherein the substitution is at least one amino acid substitution at a position that corresponds to position 17, 29, 30, 52, 86, 117, 122, 160, 163, 167, 265, 266, 286, or 289 of SEQ ID NO: 1, and wherein the variant has lipase activity.

* * * * *

UNITED STATES PATENT AND TRADEMARK OFFICE
CERTIFICATE OF CORRECTION

PATENT NO. : 7,314,739 B2
APPLICATION NO. : 10/493210
DATED : January 1, 2008
INVENTOR(S) : Markus Matuschek et al.

It is certified that error appears in the above-identified patent and that said Letters Patent is hereby corrected as shown below:

On the Front Page:
In the References Cited, under OTHER PUBLICATIONS, lines 13 and 14, insert --and-- between "γ-" and "δ-lactones".

In the Claims:
In Claim 1, column 15, starting at line 54, delete the text beginning with "A lipase variant" to and ending "has lipase activity." and replace, with the following:
--A variant having lipase activity obtained by substitution of an amino acid of a starting lipase selected from the group of lipases of homologous families I.1 or I.2, wherein an amino acid of the starting lipases located at one or more positions that correspond to positions selected from the group consisting of 17, 29, 30, 52, 86, 117, 122, 160, 163, 167, 265, 266, 286, and 289 of SEQ ID NO:1, is substituted with another amino acid.--.

In Claim 2, in column 15, line 62, "The lipase variant" should read --The variant--.

In Claim 3, in column 16, line 56, "The lipase variant" should read --The variant--; lines 62-63, "a lipase from *Pseudomonas Fragi*, with a substitution at position Leu$^7$;" should read --a lipase from *Pseudomonas fragi*, with a substitution at position Leu$^{17}$;--.

In Claim 4, in column 17, line 17, "The lipase variant" should read --The variant--; line 23, "a lipase from *Pseudomonas Fragi*," should read --a lipase from *Pseudomonas fragi*,--; line 42, insert --and-- after "Phe$^{57}$;".

In Claim 5, in column 17, line 45, "The lipase variant" should read --The variant--.

In Claim 6, in column 17, line 48, "The lipase variant" should read --The variant--.

In Claim 7, in column 18, line 12, "the lipase variant" should read --the variant--.

Signed and Sealed this
Fifteenth Day of February, 2011

David J. Kappos
*Director of the United States Patent and Trademark Office*

CERTIFICATE OF CORRECTION (continued)
U.S. Pat. No. 7,314,739 B2

In Claim 10, in column 18, line 19, "the lipase variant" should read --the variant--.

In Claim 11, in column 18, line 22, "the lipase variant" should read --the variant--.

In Claim 12, in column 18, line 25, "the lipase variant" should read --the variant--.

In Claim 13, in column 18, line 30, "the lipase variant" should read --the variant--.

In Claim 16, in column 18, line 38, "stereo isomer" should read --stereoisomer--; line 40, "the lipase variant" should read --the variant--, In Claim 18, in column 18, line 47, "the lipase variant" should read --the variant--.